US00PP33385P3

(12) United States Plant Patent
Wiegman

(10) Patent No.: US PP33,385 P3
(45) Date of Patent: Aug. 24, 2021

(54) APPLE TREE NAMED 'BINGO GALA'

(50) Latin Name: *Malus domestica*
Varietal Denomination: Bingo Gala

(71) Applicant: Golden Joy Bingo (Pty.) Ltd., Grabouw (ZA)

(72) Inventor: Jan Dawid Wiegman, Grabouw (ZA)

(73) Assignee: Golden Joy Bingo (Pty.) Ltd., Grabouw (ZA)

( * ) Notice: Subject to any disclaimer, the term of this patent is extended or adjusted under 35 U.S.C. 154(b) by 0 days.

(21) Appl. No.: 16/873,936

(22) Filed: Aug. 17, 2020

(65) Prior Publication Data

US 2021/0059089 P1 Feb. 25, 2021

Related U.S. Application Data

(60) Provisional application No. 62/922,687, filed on Aug. 21, 2019.

(51) Int. Cl.
*A01H 5/08* (2018.01)
*A01H 6/74* (2018.01)

(52) U.S. Cl.
USPC ..... Plt./162
CPC ..... *A01H 6/7418* (2018.05)

(58) Field of Classification Search
USPC ..... Plt./161, 162
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Bingo Gala' is a new apple variety discovered as a spontaneous limb mutation of 'Tenroy Gala'. The fruit of 'Bingo Gala' is notable for its attractive red overcolor, which consistently covers about eighty percent of the fruit surface. 'Bingo Gala' can be harvested in one pick.

8 Drawing Sheets

Latin name: *Malus domestica.*
Variety denomination: 'Bingo Gala'.

BACKGROUND OF THE VARIETY

'Bingo Gala' is a new and distinct variety of 'Gala'-type apple tree. The new variety is a spontaneous limb mutation of 'Tenroy Gala' (U.S. Plant Pat. No. 4,121, expired). 'Bingo Gala' was first observed in 2012 at Caledon, Republic of South Africa, in a commercial orchard planted with 'Tenroy Gala' trees, and was first asexually reproduced by grafting in 2012 in the same location. The variety has since been asexually reproduced by budding, and has been observed to remain true to type over successive asexually propagated generations.

BRIEF DESCRIPTION OF THE VARIETY

'Bingo Gala' was first selected for its attractive fruit, which has an attractive red blush over about 80% of the fruit surface. This desirable coloration has been found to occur very consistently, allowing harvest to be accomplished in a single pick. 'Bingo Gala' is distinguished from 'Tenroy Gala' and 'Bigbucks' (U.S. Plant Pat. No. 29,365) as set forth below.

TABLE 1

Comparison of 'Bingo Gala' to Parent 'Tenroy Gala'

| Characteristic | 'Bingo Gala' | 'Tenroy Gala' |
|---|---|---|
| Fruit overcolor | Red-purple | Red |
| Amount of overcolor | Blush over about 80% of surface area | Up to about 50% of surface area |

TABLE 1-continued

Comparison of 'Bingo Gala' to Parent 'Tenroy Gala'

| Characteristic | 'Bingo Gala' | 'Tenroy Gala' |
|---|---|---|
| Fruit stem color | Grey-brown | Purple |
| Leaf color near base | Red | Purple |
| Nursery tree size | 20 cm shorter than 'Tenroy Gala' | 20 cm taller than 'Bingo Gala' |

TABLE 2

Comparison of 'Bingo Gal' to 'Bigbucks'

| Characteristic | 'Bingo Gala' | 'Bigbucks' |
|---|---|---|
| Fruit overcolor | Red-purple | Dark red |
| Amount of overcolor | Blush over about 80% of surface area | Solid over about 90% to 100% of surface area |
| Fruit stem color | Red | Purple |
| Leaf color near base | Red | Purple |

BRIEF DESCRIPTION OF THE PHOTOGRAPHS

The attached photographs were taken during the 2018 and 2019 growing seasons near Caledon, Republic of South Africa. The trees shown were planted in 2013 on 'M793' rootstock (not patented).

FIG. 1 shows 'Bingo Gala' trees;
FIG. 2 shows 'Bingo Gala' fruit and leaves on the tree;
FIG. 3 shows 'Bingo Gala' fruit and leaves on the tree;
FIG. 4 shows 'Bingo Gala' fruit and leaves on the tree;
FIG. 5 shows fruit of 'Bigbucks' (left) and 'Bingo Gala' (right);

DETAILED BOTANICAL DESCRIPTION OF THE VARIETY

Figure 1:
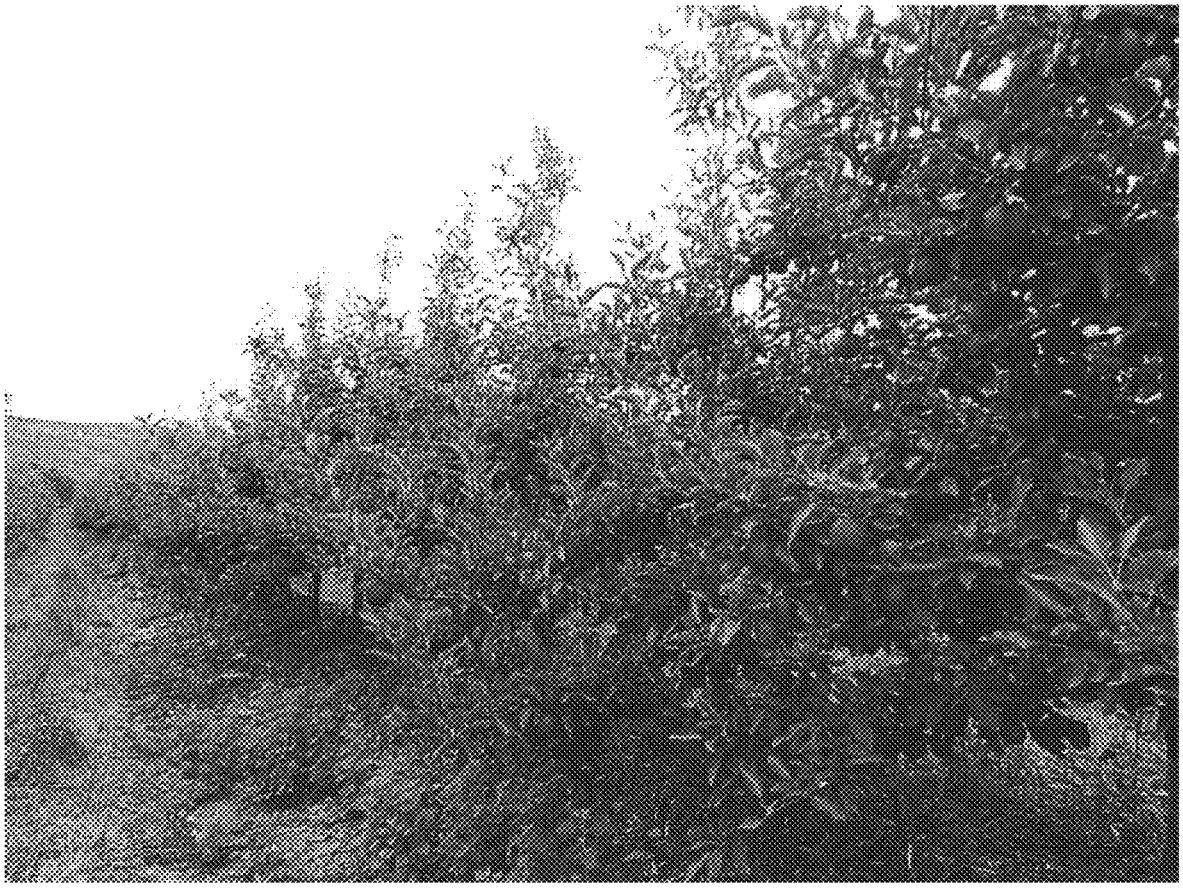
Figure 2:
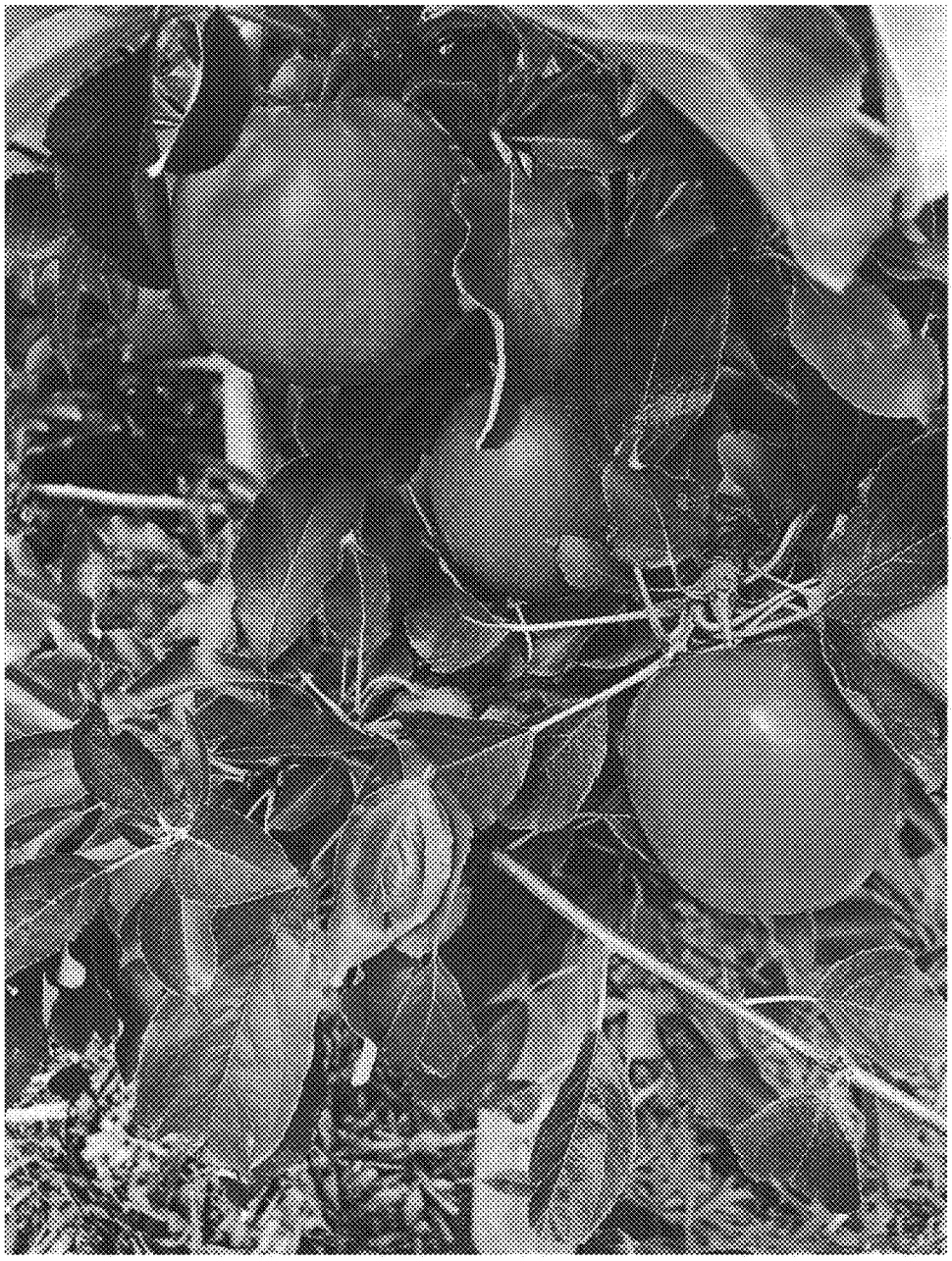
Figure 3:
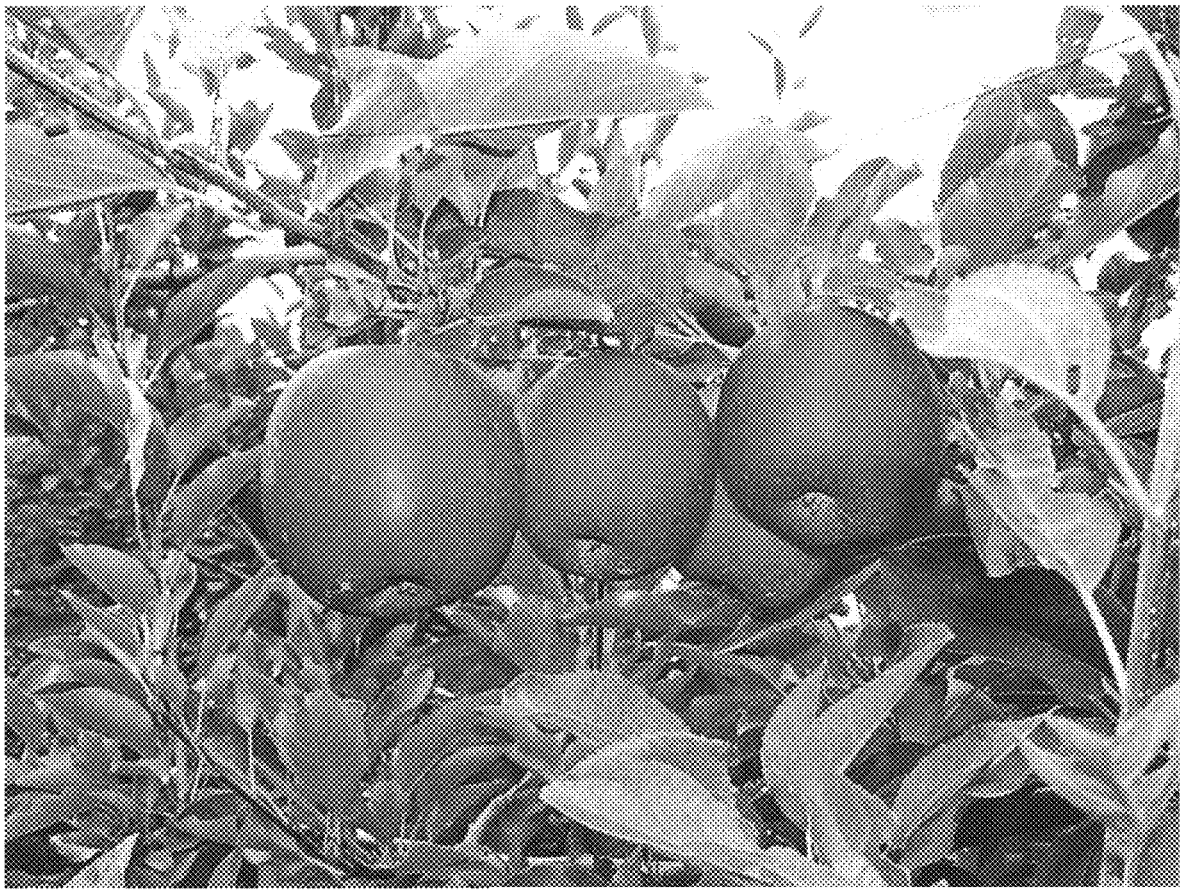
Figure 4:
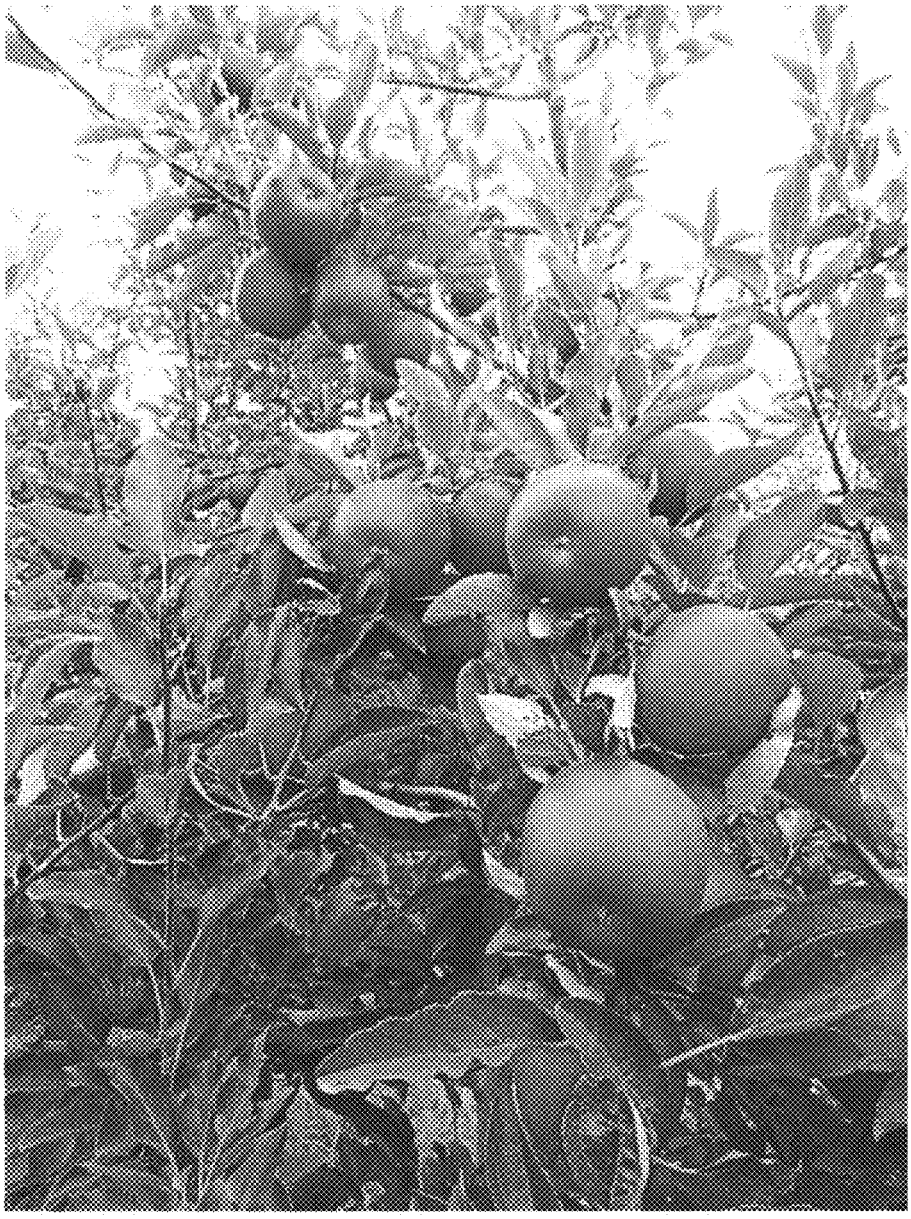
Figure 5:
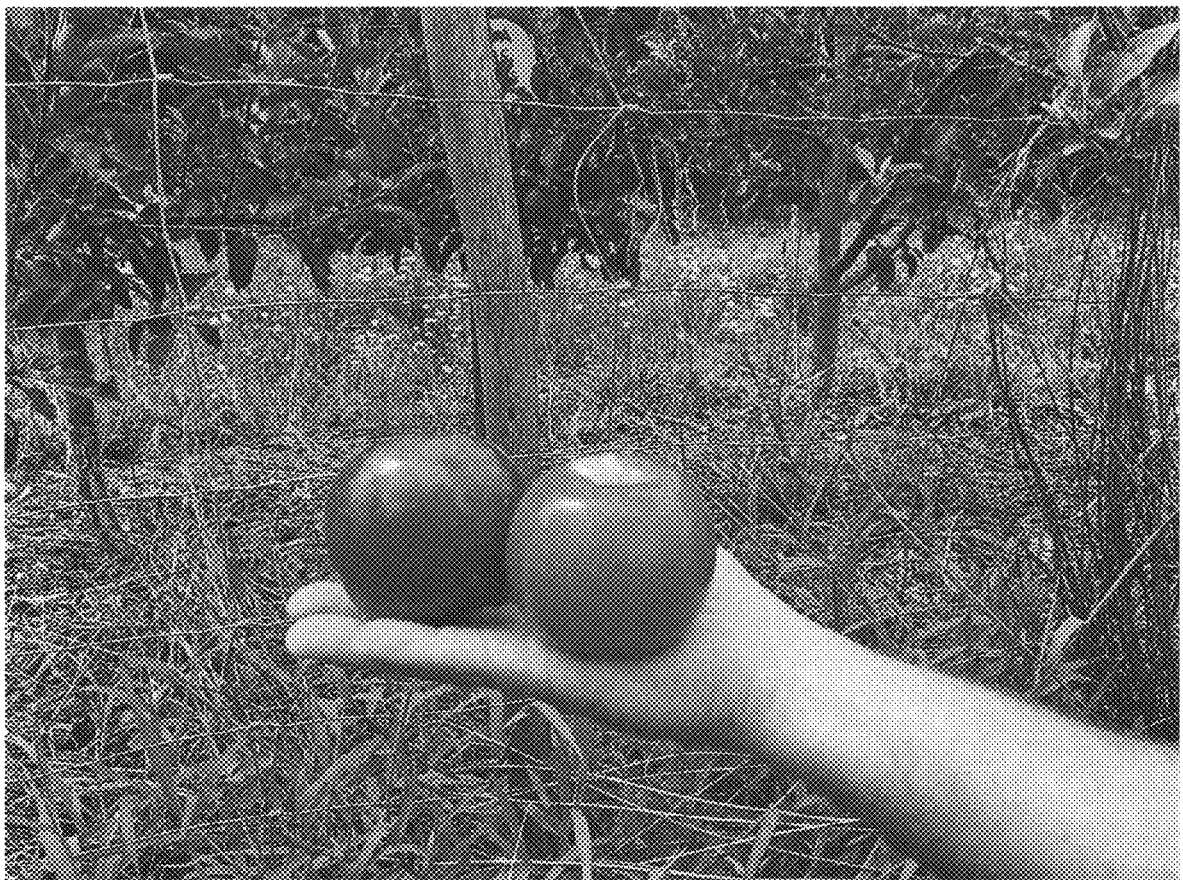
Figure 6:
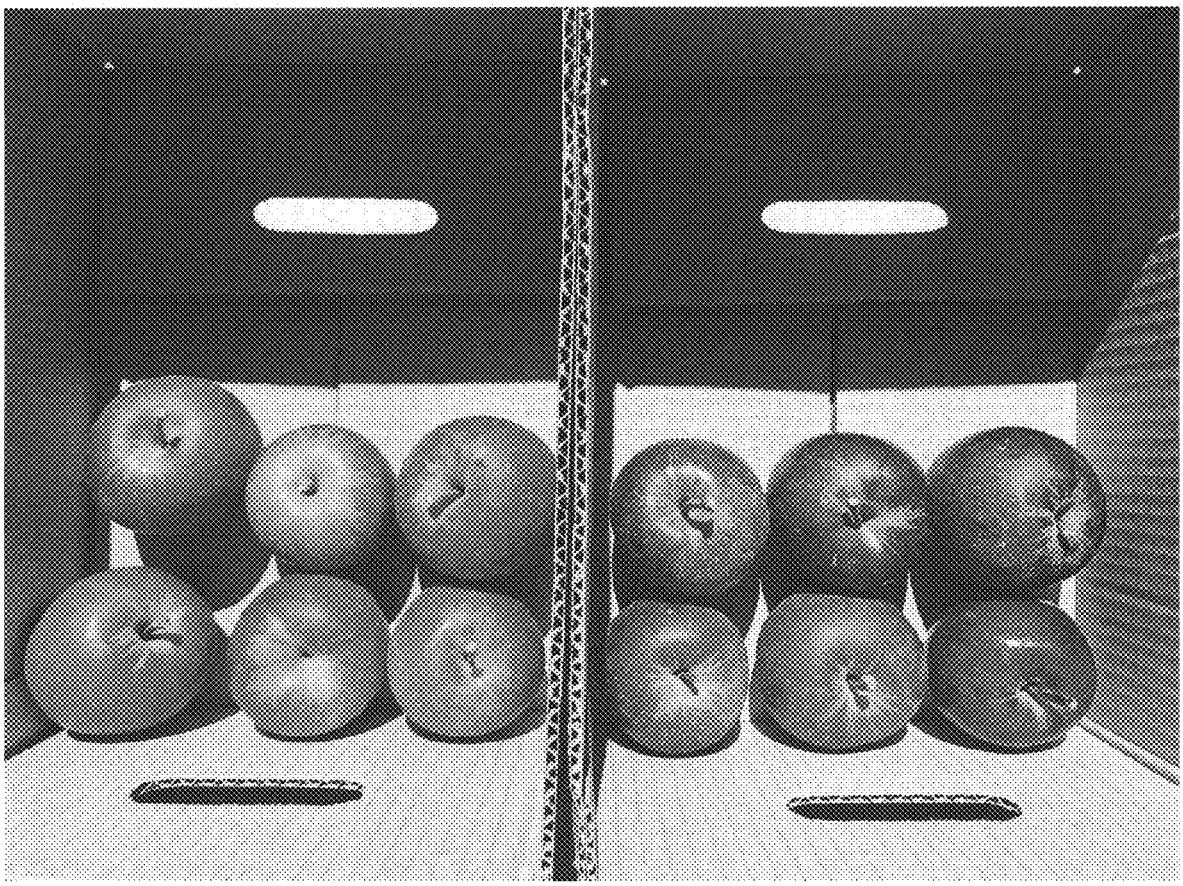
FIG. 6 shows fruit of 'Bingo Gala' (left) and 'Bigbucks' (right)
Figure 7:
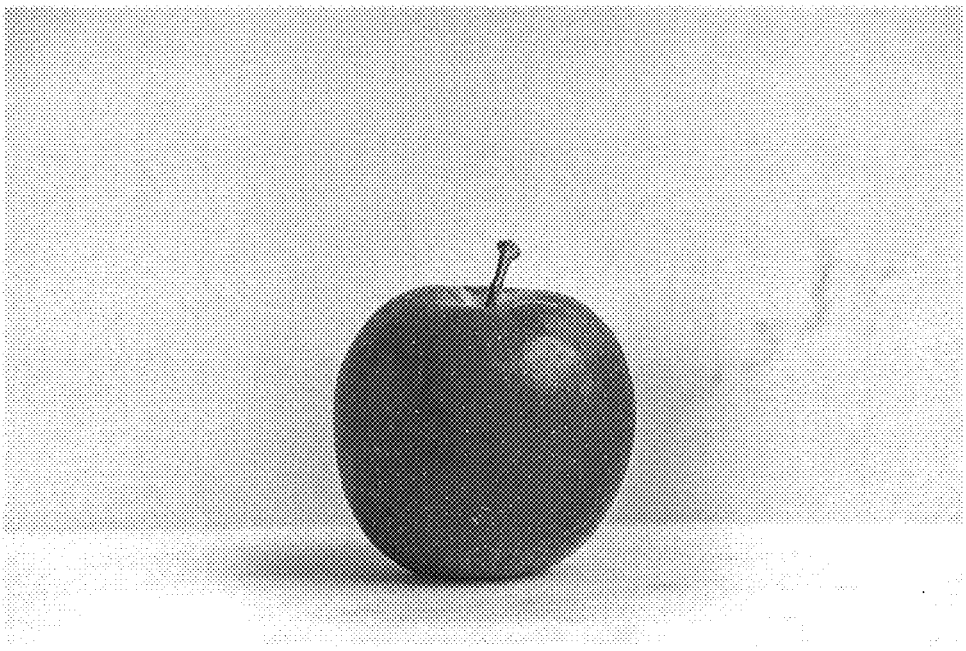
FIG. 7 shows a whole 'Bingo Gala' fruit.
Figure 8:
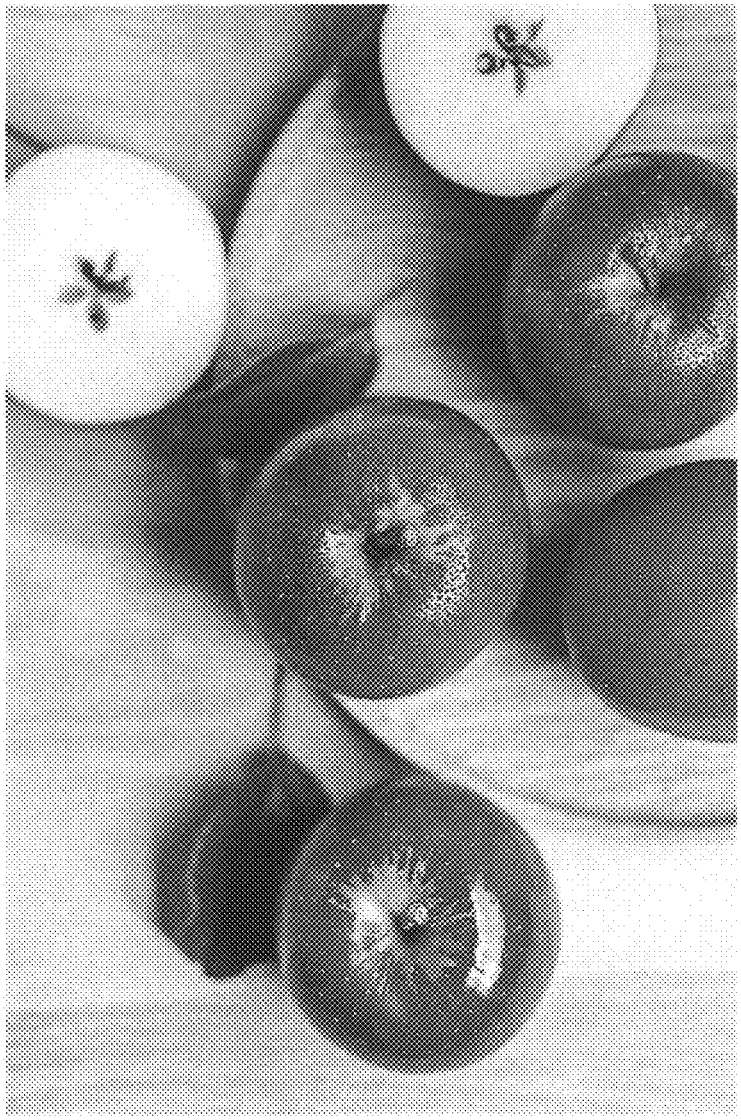
FIG. 8 shows whole and sectioned 'Bingo Gala' fruit and leaves.

The following botanical description is based primarily on observations made during the 2018 and 2019 growing seasons near Caledon, Republic of South Africa. The described trees were planted in 2013 on 'M793' rootstock. It should be understood that the characteristics described will vary somewhat depending upon cultural practices and climatic conditions, and will vary with location and season. Color descriptions are made with reference to The R.H.S. Colour Chart, 4$^{th}$ ed. (Royal Horticultural Society, 2001)

Tree:
- *Vigor*.—Strong.
- *Type*.—Ramified.
- *Habit*.—Semi-upright.
- *Height*.—3 m.
- *Trunk diameter at* 30 *cm above graft*.—15 cm.
- *Bearing*.—On shoots and spurs.
- *Bark color*.—Grey-brown 199D.
- *Bark texture*.—Smooth.
- *Lenticels*.—Not present on trunk.

Branch (fruiting branches located at around 1 m above the graft union):
- *Length*.—100 cm.
- *Diameter*.—12 mm.
- *Crotch angle*.—30° to 45°.
- *Bark color*.—Grey-brown 199D.
- *Bark texture*.—Smooth.
- *Lenticel length*.—3.1 mm.
- *Lenticel width*.—1.4 mm.
- *Lenticel shape*.—Round to elongated.
- *Lenticel color*.—Yellow-white 158A.
- *Lenticel density*.—8 per cm$^2$.

One year old shoot:
- *Length*.—50 cm.
- *Diameter*.—8 mm.
- *Pubescence*.—Weak.
- *Shoot color*.—Greyed-purple 183B.
- *Internode length*.—Short, 3 cm.
- *Lenticel shape*.—Elongated.
- *Lenticel size*.—4 mm×2 mm.
- *Lenticel color*.—Greyed white 156C.
- *Lenticel density*.—5 per cm$^2$.

Flowers:
- *Bud length*.—6 mm.
- *Bud diameter*.—4 mm.
- *Bud texture*.—Smooth.
- *Bud color*.—Greyed-purple 187A.
- *Bud shape*.—Round conical.
- *Quantity per spur*.—5 to 6.
- *Time of beginning of flowering* (*when tree presents* 10% *fully opened flowers*).—Mid-season (Sep. 20, 2019).
- *Date of full bloom*.—Mid-season (Oct. 15, 2019).
- *Pollination requirement*.—Pollinator such as 'Granny Smith' (not patented), 'Golden Delicious' (not patented) required.
- *Diameter of fully open flower*.—Medium, 40 mm.
- *Depth of fully open flower*.—19 mm.
- *Fragrance*.—None.
- *Quantity of petals*.—5.
- *Relative position of petal margin*.—Not touching.
- *Petal shape*.—Elliptic.
- *Petal apex*.—Round.
- *Petal base*.—Pointed.
- *Petal margin*.—Smooth.
- *Petal texture*.—Both surfaces smooth.
- *Petal length*.—24 mm.
- *Petal width*.—19 mm.
- *Petal color, upper surface*.—White 155C with streaks of red 54C.
- *Petal color, lower surface*.—White 155C.

Sepals:
- *Quantity*.—5 per flower.
- *Shape*.—Pointed.
- *Apex*.—Pointed.
- *Margin*.—Smooth.
- *Texture*.—Both surfaces smooth.
- *Length*.—6 mm.
- *Color*.—Both surfaces green 142B.

Pistils:
- *Quantity*.—6.
- *Length*.—10 mm.
- *Color*.—Yellow-green 145A.

Stigma:
- *Length*.—1 mm.
- *Color*.—Yellow-green 145A.

Style:
- *Length*.—3 mm.
- *Color*.—Yellow-green 145A.

Ovary:
- *Length*.—5 mm.
- *Width*.—1.5 mm.
- *Color*.—Yellow-green 144A.

Anthers:
- *Quantity*.—8.
- *Length*.—7 mm.
- *Diameter*.—1 mm.
- *Color*.—Yellow 10A.
- *Pollen quantity*.—Abundant.
- *Pollen color*.—Yellow 10A.

Leaves:
- *Shape*.—Ovate to elliptic.
- *Length*.—Medium, 93 mm.
- *Width*.—Narrow, 51 mm.
- *Length/width ratio*.—Large, 1.8.
- *Blade margin*.—Serrate.
- *Apex shape*.—Acuminate.
- *Base shape*.—Cuneate.
- *Texture*.—Both surfaces smooth.
- *Color of upper surface*.—Green 137A with red-purple 59B near petiole.
- *Color of lower surface*.—Green 138B with red-purple 59B near petiole.
- *Attitude in relation to shoot*.—Upwards.

Petiole:
- *Length*.—Long, 37 mm.
- *Diameter*.—2.2 mm.
- *Texture*.—Smooth.
- *Color*.—Red-purple 59B.

Fruit:
- *Quantity per cluster*.—1 to 3.
- *Diameter*.—Medium, 72 mm.
- *Height*.—Medium, 67 mm.

*Weight.*—182 g.
*Ratio of height to width.*—Medium, 0.92.
*General shape in profile.*—Globose.
*Position of maximum diameter.*—Middle.
*Ribbing.*—Absent or very weak.
*Crowning at calyx end.*—Weak.
*Size of eye.*—Medium.
*Aperture of eye.*—Closed.
*Bloom of skin.*—Medium.
*Greasiness of skin.*—Absent.
*Background color of skin.*—Yellow 11C.
*Over color of skin.*—Red-purple 60B.
*Amount of over color.*—Very high.
*Intensity of over color.*—High.
*Pattern of over color.*—Only solid blush.
*Amount of russet around stalk cavity.*—Absent or small.
*Amount of russet on cheeks.*—Absent or small.
*Area of russet around eye basin.*—Absent or small.
*Length of stalk.*—25 mm.
*Thickness of stalk.*—3 mm.
*Stalk color.*—Red.
*Depth of stalk cavity.*—Deep, 16 mm.
*Width of stalk cavity.*—Narrow, 30 mm.
*Depth of eye basin.*—Shallow, 7 mm.
*Width of eye basin.*—Very narrow, 26 mm.
*Firmness of flesh.*—Medium, 7.5 kg.
*Flesh texture.*—Crisp.
*Quantity of locules.*—6.
*Aperture of locules.*—Moderately open.
*Locule width.*—18 mm.
*Aroma.*—Good.
*Juiciness.*—High.
*Brix.*—15° Brix.
*Flesh color.*—Yellow 11D.
*Quantity of seeds per fruit.*—About 10, similar to 'Tenroy Gala'.
*Seed shape.*—Elliptic.
*Seed length.*—4 mm.
*Seed width.*—2 mm.
*Seed color.*—166A greyed-orange.
*Eating quality of fruit.*—Excellent.
*Harvest maturity.*—Early (early to mid-February; Feb. 21, 2019).
*Harvest yield.*—36 kg per tree (2019).
*Resistance to pests and diseases.*—Typical of 'Gala'-types.
*Storage characteristics.*—Typical of 'Gala'-types.

Market use: Fresh.

I claim:

1. A new and distinct apple tree substantially as described and illustrated herein.

* * * * *